(12) United States Patent
Cho et al.

(10) Patent No.: US 7,561,659 B2
(45) Date of Patent: Jul. 14, 2009

(54) METHOD FOR RECONSTRUCTING A LOCAL HIGH RESOLUTION X-RAY CT IMAGE AND APPARATUS FOR RECONSTRUCTING A LOCAL HIGH RESOLUTION X-RAY CT IMAGE

(76) Inventors: Min-Hyoung Cho, 803-1603 Byoukjeok Doosan A.P.T., Youngtong-dong, Youngtong-gu, Suwon-si, Gyeonggi-do 122-050 (KR); Soo-Yeol Lee, 04-304 Hayan Maeul Grand Villa, Gumi-dong, Bundang-gu, Sungnam-si, Gyeonggi-do 463-793 (KR); In-Kon Chun, 109-1006 Mugunghwa Joogong A.P.T., Geumjeong-dong, Gunpo-si, Gyeonggi-do 435-050 (KR); Sang-Chul Lee, #613 Daelim Rezion A.P.T., Seocho 1-dong, Seocho-gu, Seoul 137-071 (KR)

( * ) Notice: Subject to any disclaimer, the term of this patent is extended or adjusted under 35 U.S.C. 154(b) by 0 days.

(21) Appl. No.: 11/781,141

(22) Filed: Jul. 20, 2007

(65) Prior Publication Data
US 2008/0118024 A1 May 22, 2008

Related U.S. Application Data

(63) Continuation of application No. PCT/KR2005/001815, filed on Jun. 14, 2005.

(30) Foreign Application Priority Data
Jan. 21, 2005 (KR) .................. 10-2005-0005831

(51) Int. Cl.
*A61B 6/00* (2006.01)
(52) U.S. Cl. ............................ 378/13; 378/4
(58) Field of Classification Search .................. 378/4, 378/13
See application file for complete search history.

(56) References Cited

U.S. PATENT DOCUMENTS 4,029,963 A * 6/1977 Alvarez et al. ................ 378/5

(Continued)

FOREIGN PATENT DOCUMENTS

JP 12-325338 A 11/2000

OTHER PUBLICATIONS

Ogawa et al., A Reconstruction Algorithm from Truncated Projections, IEEE Transactions on Medical Imaging, vol. MI-3, No.1, Mar. 1984, pp. 34-40.*
International Search Report regarding PCT Application No. PCT/KR2005/001815 dated Oct. 27, 2005.

*Primary Examiner*—Edward J Glick
*Assistant Examiner*—Alexander H Taningco
(74) *Attorney, Agent, or Firm*—Knobbe Martens Olson & Bear LLP (57) ABSTRACT

Disclosed is a method for reconstructing an X-ray CT (computerized tomography) image. The method includes acquiring projection data by means of irradiation of X-rays on a target object at a position close to an X-ray generator such that a portion of the target object including a local region of interest exists within a range of irradiation angles of X-rays, calculating virtual projection data on the assumption that the X-rays are irradiated on the entire target object at the close position, based on projection data acquired through irradiation of the X-rays on the entire target object at a position where the entire target object exists within the range of irradiation angles of X-rays, combining the virtual projection data on the entire target object except data on the local region of interest with the projection data acquired at the position close to the X-ray generator, and reconstructing the combined projection data.

20 Claims, 11 Drawing Sheets

U.S. PATENT DOCUMENTS

| | | | | |
|---|---|---|---|---|
| 4,200,799 | A * | 4/1980 | Saito | 378/13 |
| 4,418,387 | A * | 11/1983 | Yamaguchi et al. | 378/11 |
| 4,550,371 | A * | 10/1985 | Glover et al. | 378/4 |
| 5,475,726 | A * | 12/1995 | Azevedo et al. | 378/4 |
| 5,598,453 | A * | 1/1997 | Baba et al. | 378/146 |
| 6,307,909 | B1 * | 10/2001 | Flohr et al. | 378/4 |
| 6,826,251 | B1 | 11/2004 | Miyazaki et al. | |
| 7,397,887 | B2 * | 7/2008 | Kuhn | 378/9 |
| 2002/0191736 | A1 * | 12/2002 | Shiota | 378/4 |
| 2005/0111623 | A1 * | 5/2005 | Bruder et al. | 378/95 |

* cited by examiner

METHOD FOR RECONSTRUCTING A LOCAL HIGH RESOLUTION X-RAY CT IMAGE AND APPARATUS FOR RECONSTRUCTING A LOCAL HIGH RESOLUTION X-RAY CT IMAGE

CROSS-REFERENCE TO RELATED PATENT APPLICATIONS

This application is a continuation application under 35 U.S.C. § 365(c) of International Application No. PCT/KR2005/001815, filed Jun. 14, 2005 designating the United States. International Application No. PCT/KR2005/001815 was published in English as WO2006/078085 A1 on Jul. 27, 2006. This application further claims the benefit of the earlier filing date under 35 U.S.C. § 365(b) of Korean Patent Application No. 10-2005-0005831 filed Jan. 21, 2005. This application incorporates herein by reference the International Application No. PCT/KR2005/001815 including the International Publication No. WO2006/078085 A1 and the Korean Patent Application No. 10-2005-0005831 in their entirety.

BACKGROUND

1. Field

The present disclosure relates to a method and apparatus for reconstructing an X-ray CT (computerized tomography) image, and more particularly, to a method and apparatus for reconstructing an X-ray CT image having high resolution locally.

2. Discussion of the Related Technology

When X-rays pass through an object, they show a property by which the intensity thereof decreases according to the physical property and length of the object. The property of the X-rays is described by "Lambert-Beer's Law" that is expressed as the following equation:

$$I = I_0 e^{-\mu L} \tag{1}$$

where $I_0$ is the initial intensity of X-rays, $\mu$ is a unique X-ray attenuation coefficient of an object, and L is the length of the object through which the X-rays pass. This equation shows a relationship in which upon irradiation of X-rays with an initial intensity of $I_0$, the X-rays are attenuated according to the attenuation coefficient and distance of the object through which the X-rays pass. This equation is applied to a case where the object comprises a single substance. In case of an object with a variety of substances mixed therein, the following equation is applied thereto:

$$I = I_0 e^{-\int_0^L \mu(s) ds} \tag{2}$$

where s is a path of X-rays, and $\mu(s)$ is an X-ray attenuation coefficient and is a function of a path since it varies according to locations in an object.

An X-ray system, which has been widely used for a non-destructive inspection for diagnosing the interior of a human body or finding a defect within an object, obtains a projection image by catching the intensity of X-rays, which varies according to locations on an object though which the X-rays pass, on a two-dimensional film. When X-rays pass through an object, the intensity of the X-rays varies according to the unique attenuation coefficient of the object and the path on which the X-rays travel, as expressed by the equations. The varying values are detected by a photosensitive film. Since such an X-ray projection photograph represents a final cumulative value obtained during passage of X-rays on a path within an object, it shows information on the interior of the object but has a disadvantage in that it cannot show information on the depth of the object, i.e., cross-sectional images.

Figure 1:
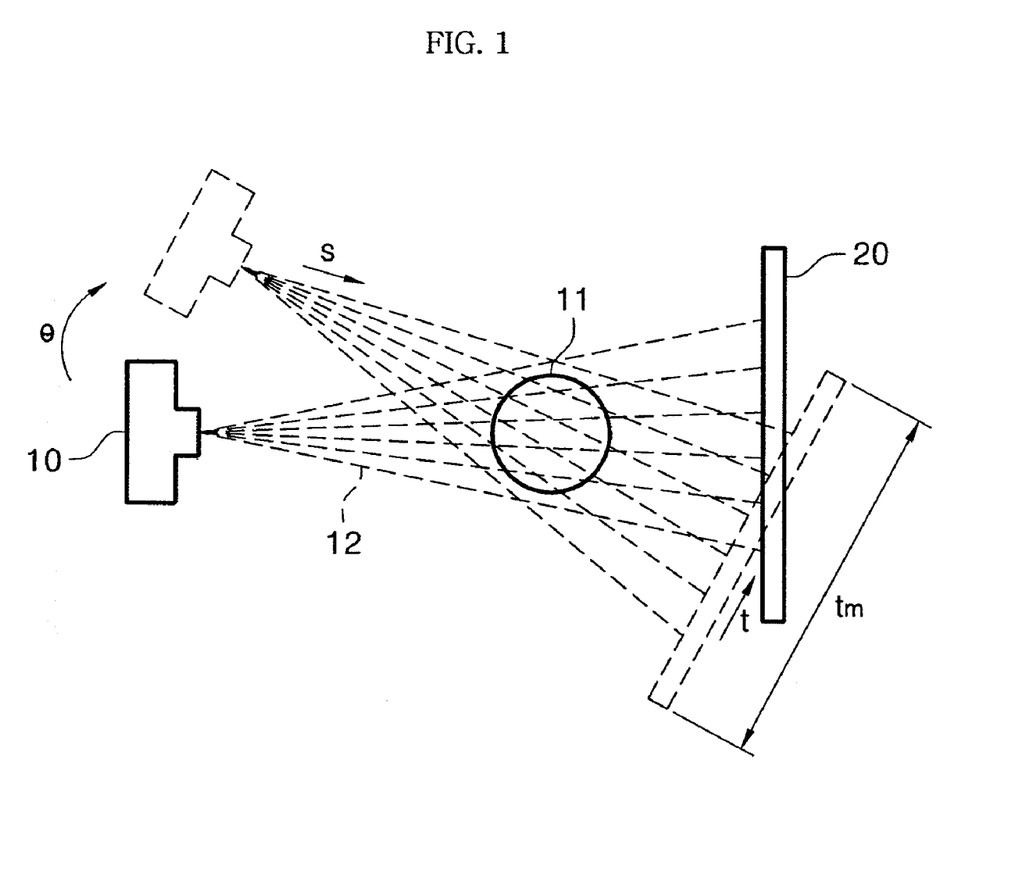
FIG. 1 is a view illustrating an operational principle of an apparatus for reconstructing an X-ray CT image.

On the contrary, an apparatus for reconstructing an X-ray CT image obtains several ten to several hundred projection images at various angles by rotating an object through 360 degrees or rotating an X-ray generator and a detector through 360 degrees around an object, and mathematically reconstructs the images using a computer to create information on the depth of the object, i.e., cross-sectional images. FIG. 1 is a schematic view illustrating an operational principle of an exemplary apparatus for reconstructing an X-ray CT image. The exemplary apparatus for reconstructing an X-ray CT image is configured to reconstruct CT images by rotating an X-ray generator 10 and an X-ray detector 20, which are installed to be spaced apart from a target object 11 of which CT images will be obtained and to face the target object, through 360 degrees around the target object 11, by generating X-rays 12 from the X-ray generator 10 at a predetermined angular interval, and by causing the X-ray detector 20 to detect the X-rays 12 that have passed through the target object 11. The most general method for creating cross-sectional images from data detected by the X-ray detector 20 is a back projection method, and its associated equations are as follows:

$$\mu(x, y) = \frac{1}{2}\int_0^{2\pi} \int_{-\frac{1}{2}t_m}^{\frac{1}{2}t_m} P_\theta(t) h(x\cos\theta + y\sin\theta - t) dt d\theta \tag{3}$$

$$P_\theta(t) = -\log\frac{I}{I_0} = \int_0^{L(t)} \mu(s, t) ds \tag{4}$$

where $\theta$ and t are geometric conditions for acquisition of projection data and indicate a rotational angle and coordinates along the length of the X-ray detector 20, respectively, and $t_m$ is the total length of the detector 20. $P_\theta(t)$ is projection data obtained in the direction of $\theta$. The function $h(x\cos\theta + y\sin\theta - t)$ indicates a back projection filtering function. Generally, a Ram-Lak filter, a Shepp-Logan or the like is widely used. A function $\mu(x,y)$ that is desired to be obtained through calculation of such a back projection process is an attenuation coefficient at each of locations of a target object, which represents how much X-rays are attenuated upon passage thereof through the object. The function means desired cross-sectional images. Consequently, the apparatus for reconstructing an X-ray CT image quantitatively calculates unique attenuation coefficients at respective locations according to the kind of object when X-rays pass through cross sections of an object, and shows the calculated results as images.

Figure 2:
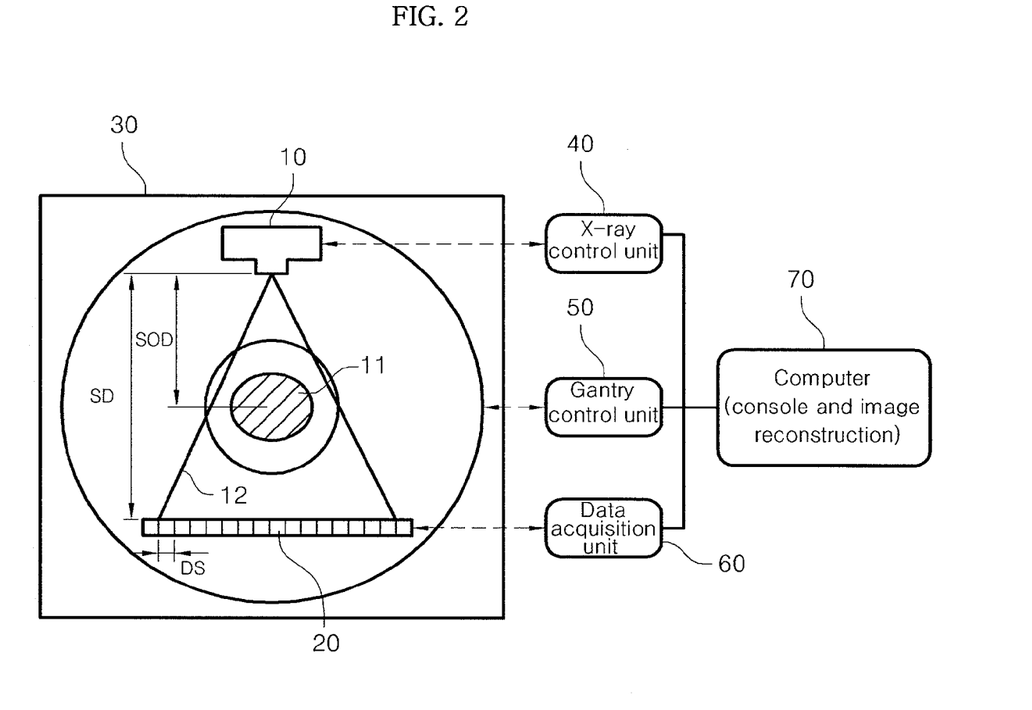
FIG. 2 is a schematic view showing a basic configuration of an exemplary apparatus for reconstructing an X-ray CT image.

FIG. 2 is a schematic view showing a basic configuration of an apparatus for reconstructing an X-ray CT image, which is mainly used at present. As shown in FIG. 2, the exemplary apparatus for reconstructing an X-ray CT image has an X-ray generator 10 and an X-ray detector 20, which are secured on a rotatably installed gantry 30. The X-ray generator 10 and the X-ray detector 20 are fixedly installed at opposite positions with respect to a rotational center of the gantry 30 such that they are equidistantly spaced apart from the rotational center. An X-ray detector 20 of an early apparatus for reconstructing a CT image is constructed in a one-dimensional arrangement in the form of a line to mainly obtain two-dimensional cross-sectional images. Recently, with the development of hardware technology, the X-ray detector 20 is developed from the one-dimensional arrangement in the form of a line to a limited two-dimensional arrangement in the form of several to several tens of lines. Thus, an obtained image is developed to a limited three-dimensional image. Further, there is a recent tendency for an X-ray detector to be gradually developed to a complete two-dimensional arrangement.

The resolution R of a cross-sectional image obtained by the apparatus for reconstructing an X-ray CT image constructed as above is determined according to a relative ratio of the distance from the X-ray generator 10 to the X-ray detector 20, i.e., a source to detector distance (SD), and the distance from the X-ray generator 10 to the center of a target object 11, i.e., a source to object distance (SOD). The resolution R can be expressed as the following equation. Here, "DS" is a pixel size of the X-ray detector 20.

$$R = \frac{SOD \times DS}{SD} \quad (5)$$

In the exemplary apparatus for reconstructing an X-ray CT image, an X-ray detector with a fixed pixel size is used, the distance between the X-ray generator and the X-ray detector is fixed, and the center of a target object is placed at the center between the X-ray generator and the X-ray detector. Therefore, the exemplary apparatus for reconstructing an X-ray CT image always provides only a cross-sectional image with a fixed pixel size.

Figure 3:
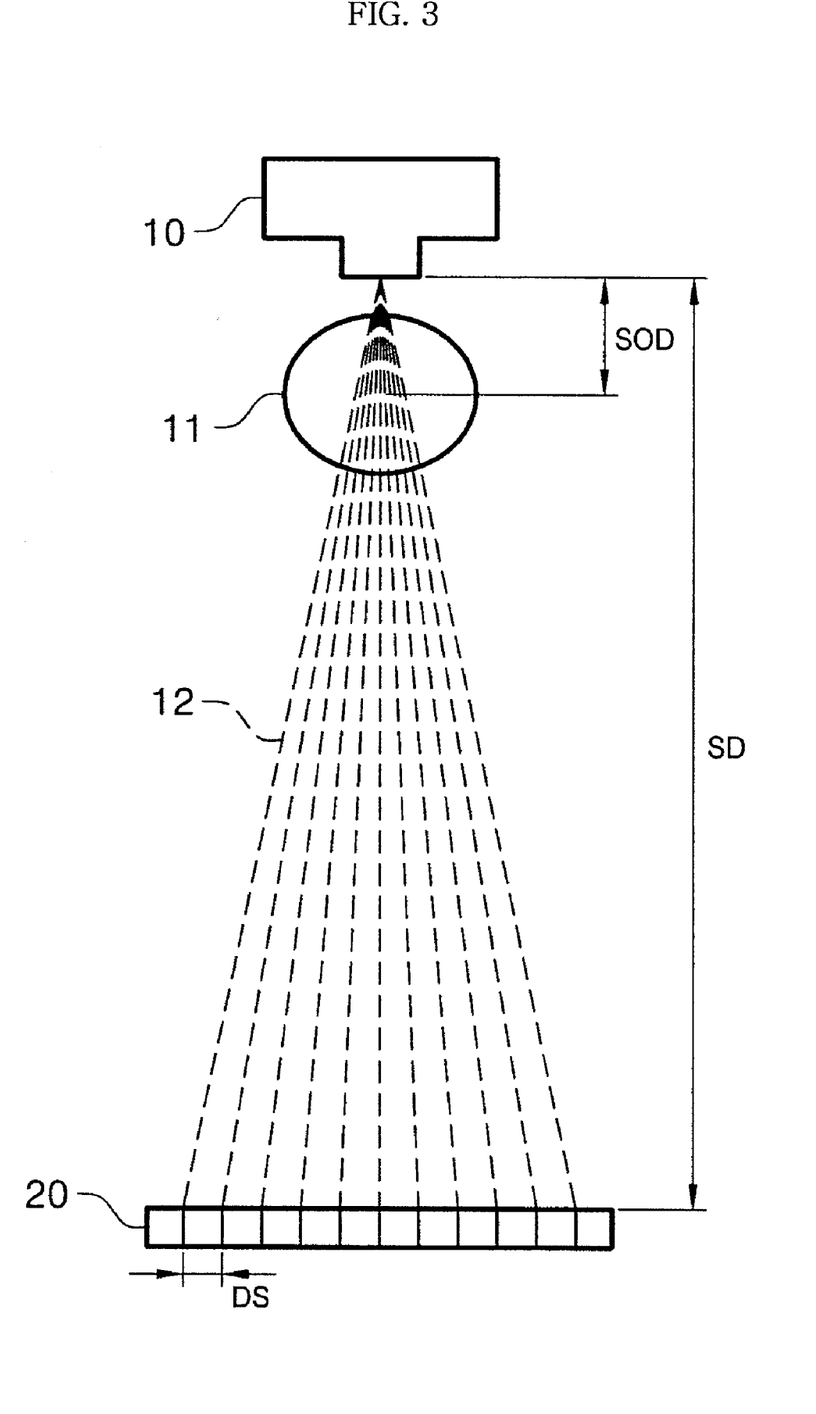
FIG. 3 is a view illustrating a principle of acquisition of a high resolution image for a local region of interest.

To obtain a high resolution cross-sectional image using the apparatus for reconstructing a CT image with a fixed pixel size, it is possible to utilize magnification effects that are obtained by moving the target object toward the X-ray generator to obtain a cross-sectional image. As shown in FIG. 3, the magnification effects refer to effects by which the resolution of data projected on the X-ray detector is improved since X-rays 12 passing through the interior of the target object 11 placed close to the X-ray generator 10 are denser than those passing through the interior of the target object 11 placed close to the X-ray detector 20. That is, a portion of the target object is placed close to the X-ray detector and thus is magnified and projected on the X-ray detector, thereby improving the resolution.

However, there is a problem in that the movement of the target object toward the X-ray generator for improving the resolution through the magnification effects causes a portion of the target object to deviate from a range of irradiation angles between the X-ray generator and the X-ray detector. Basically, in a method for reconstructing a CT image, the entire target object of which an image is to be reconstructed should be included in the range of irradiation angles of X-rays between the X-ray generator and the X-ray detector. Therefore, if a portion of the target object 11 deviates from the range of irradiation angles of X-rays as shown in FIG. 3, projection data acquired by the X-ray detector 20 do not include projection data on the portion of the target object that deviates from the range of irradiation angles, so that a complete cross-sectional image cannot be reconstructed. Accordingly, if it is intended to obtain a high resolution cross-sectional image using the magnification effects, there is a problem in that a target object is limited to a small target object which can be fully included in a range of irradiation angles of X-rays even though the target object is placed close to an X-ray generator. This problem is common to both an apparatus with a fan-beam X-ray generator and an apparatus with a cone-beam X-ray generator if it is intended to improve the resolution of a cross-sectional image using the magnification effects.

Meanwhile, U.S. Pat. No. 6,246,742 entitled "Local CT image reconstruction with limited x-ray exposure" discloses a method for obtaining a CT image by locally exposing only a desired portion of a target object to X-rays while controlling an irradiation angle of X-rays of an X-ray generator so that a CT image for the portion exposed to the X-rays can be obtained. However, as for the resolution of a local CT image obtained by means of the method disclosed in the patent, the CT image is a cross-sectional image with a resolution predetermined upon manufacture of an apparatus. It is not possible to obtain a local high resolution CT image.

There is a case where a local high resolution CT image is required for an accurate diagnosis of a specific part of a patient or clinical study. However, as discussed above, all the exemplary apparatuses for reconstructing an X-ray CT image have limitations in that they can provide only a cross-sectional image with a resolution predetermined upon manufacture of the apparatuses and thus cannot provide a local cross-sectional image with a proper resolution as desired.

The foregoing discussion is to provide general background information, and does not constitute an admission of the prior art.

SUMMARY

An aspect of the present invention provides a method for reconstructing an X-ray CT image for a target object, wherein it is possible to include a high resolution CT image for a local region of interest on the target object.

An aspect of the present invention provides an apparatus for reconstructing an X-ray CT image, wherein the distance between a target object and an X-ray generator can be controlled to reconstruct a high resolution CT image for a local region of interest on the target object.

A method for reconstructing a CT image including a high resolution X-ray CT image for a local region of interest according to an aspect of the present invention comprises the steps of acquiring projection data by means of irradiation of X-rays on a target object at a position close to an X-ray generator such that a portion of the target object including a local region of interest exists within a range of irradiation angles of X-rays; calculating virtual projection data on the assumption that the X-rays are irradiated on the entire target object at the close position, based on projection data acquired through irradiation of the X-rays on the entire target object at a position where the entire target object exists within the range of irradiation angles of X-rays; combining the virtual projection data on the entire target object except data on the local region of interest with the projection data acquired at the position close to the X-ray generator; and reconstructing the combined projection data.

Further, the step of calculating the virtual projection data may comprise the steps of reconstructing cross-sectional image data on the entire target object, based on the projection data acquired through irradiation of the X-rays on the entire target object at the position where the entire target object exists within the range of irradiation angles of X-rays; and calculating the virtual projection data through line integral for the reconstructed cross-sectional image data on the entire target object on the assumption that the X-rays are irradiated on the entire target object at the close position.

An apparatus capable of reconstructing a high resolution X-ray CT image for a local region of interest on a target object according to another aspect of the present invention includes a rotatably installed gantry, an X-ray generator installed on the gantry, an X-ray detector installed on the gantry to output projection data by detecting X-rays radiated from the X-ray generator and passed through the target object, and an imaging system for reconstructing an image of the target object by receiving the projection data from the X-ray detector. The apparatus further comprises a moving means for relatively moving any one of the X-ray generator and the target object. The imaging system receives projection data acquired by means of irradiation of the X-rays on the target object at a position close to the X-ray generator such that a portion of the target object including a local region of interest exists within a range of irradiation angles of X-rays, calculates virtual projection data on the assumption that the X-rays are irradiated on the entire target object at the close position, based on projection data acquired through irradiation of the X-rays on the entire target object at a position where the entire target object exists within the range of irradiation angles of X-rays, combines the virtual projection data on the entire target object except data on the local region of interest with the projection data acquired by means of the irradiation on the target object at the position close to the X-ray generator, and reconstructing the combined projection data into an image.

Moreover, in the apparatus for reconstructing an X-ray CT image according to an embodiment of the present invention, the imaging system performs may reconstruct cross-sectional image data on the entire target object, based on the projection data acquired through the irradiation of the X-rays on the entire target object at the position where the entire target object exists within the range of irradiation angles of X-rays, and calculate the virtual projection data through line integral for the reconstructed cross-sectional image data on the entire target object on the assumption that the X-rays are irradiated on the entire target object at the close position.

Furthermore, in the apparatus for reconstructing an X-ray CT image according to an embodiment of the present invention, the moving means may be a linearly moving means capable of moving the X-ray generator relative to the target object along a line passing through a rotational center of the gantry. Alternatively, the linearly moving means may simultaneously move the X-ray generator and the X-ray detector such that the X-ray generator and the X-ray detector are not moved relative to each other.

An apparatus capable of controlling resolution for reconstructing an X-ray CT image according to a further aspect of the present invention includes a rotatably installed gantry, an X-ray generator installed on the gantry, an X-ray detector installed on the gantry to output projection data by detecting X-rays radiated from the X-ray generator and passed through a target object, and an imaging system for reconstructing an image of the target object by receiving the projection data from the X-ray detector. The apparatus further comprises a linearly moving means for relatively moving at least one of the X-ray generator, the target object and the X-ray detector along a line passing through a rotational center of the gantry, thereby controlling the resolution of the X-ray CT image.

In the apparatus capable of controlling resolution for reconstructing an X-ray CT image according to an embodiment of the present invention, the linearly moving means may be configured to move the X-ray generator and the X-ray detector relative to the target object.

Further, the X-ray detector of the apparatus for reconstructing an X-ray CT image according to an embodiment of the present invention may be constructed in either of a one-dimensional arrangement and a two-dimensional arrangement.

| Brief Explanation of Reference Numerals in the Drawings | |
|---|---|
| 10: X-ray generator | 20: X-ray detector |
| 30: Gantry | 40: X-ray control unit |
| 50: Gantry motor control unit | 60: Data acquisition unit |
| 70: Computer | 80: Linear actuator control unit |
| 90: Linear actuator | |

DETAILED DESCRIPTION OF EMBODIMENTS

Hereinafter, embodiments of the present invention will be described in detail with reference to the accompanying drawings.

FIGS. 4 to 7 schematically show a method for reconstructing a CT image including a local high resolution X-ray CT image for a local region of interest according to an embodiment of the present invention.

Figure 4:
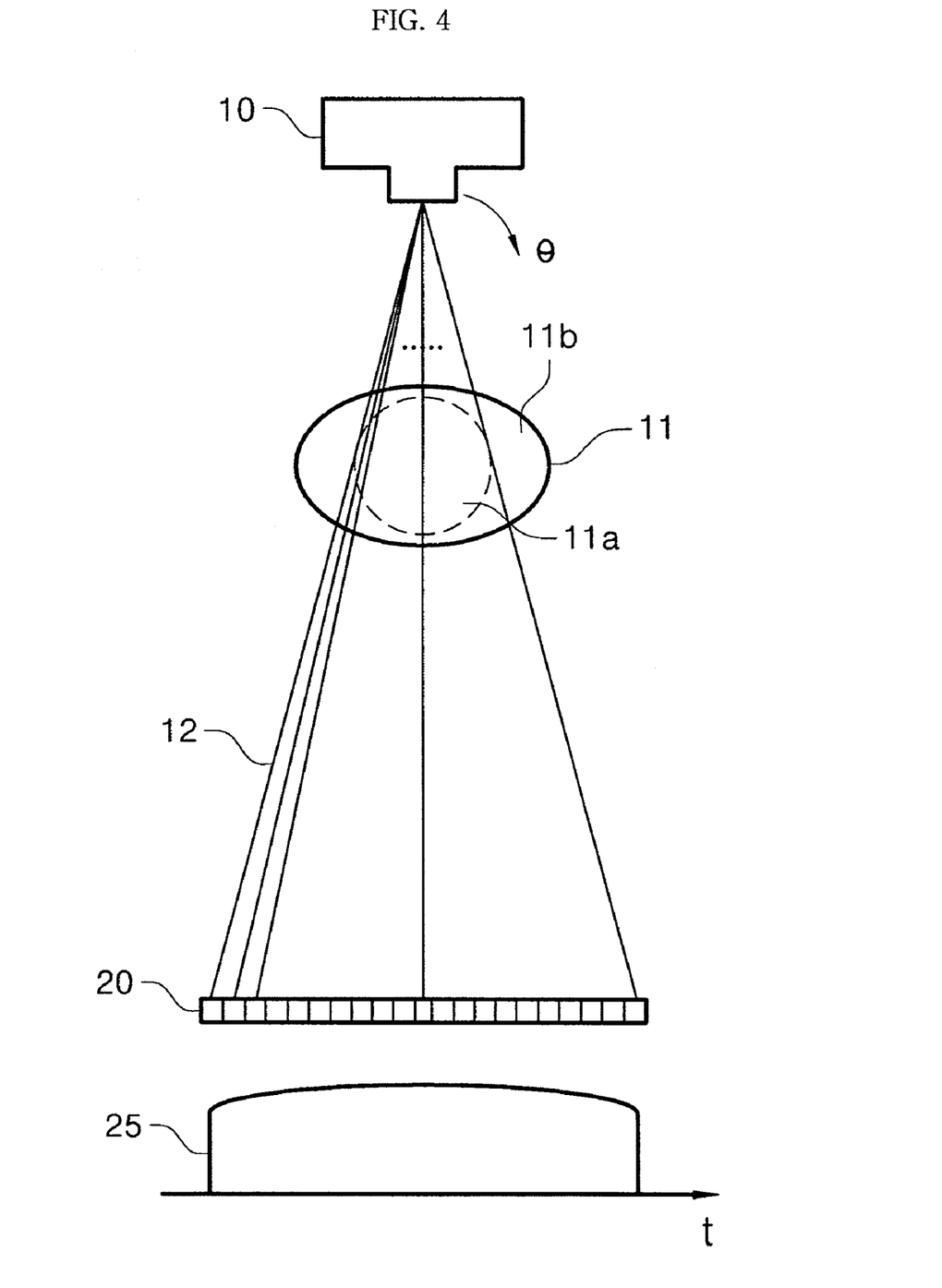
FIGS. 4 to 7 are views illustrating processes for reconstructing a local high resolution X-ray CT image according to an embodiment of the present invention.

First, as shown in FIG. 4, an object 11 is placed close to an X-ray generator 10 such that X-rays can be irradiated on a local region of interest (ROI) 11a of which a high resolution CT image is desired to be obtained on the object 11, and the X-rays are irradiated thereon, thereby acquiring high resolution projection data 25 through 360° scanning. Since the high resolution projection data 25 thus acquired do not include projection data on a portion 11b of the target object 11 existing outside a range of irradiation angles of X-rays, reconstruction of a CT image from the projection data causes severe image distortion.

Figure 5:
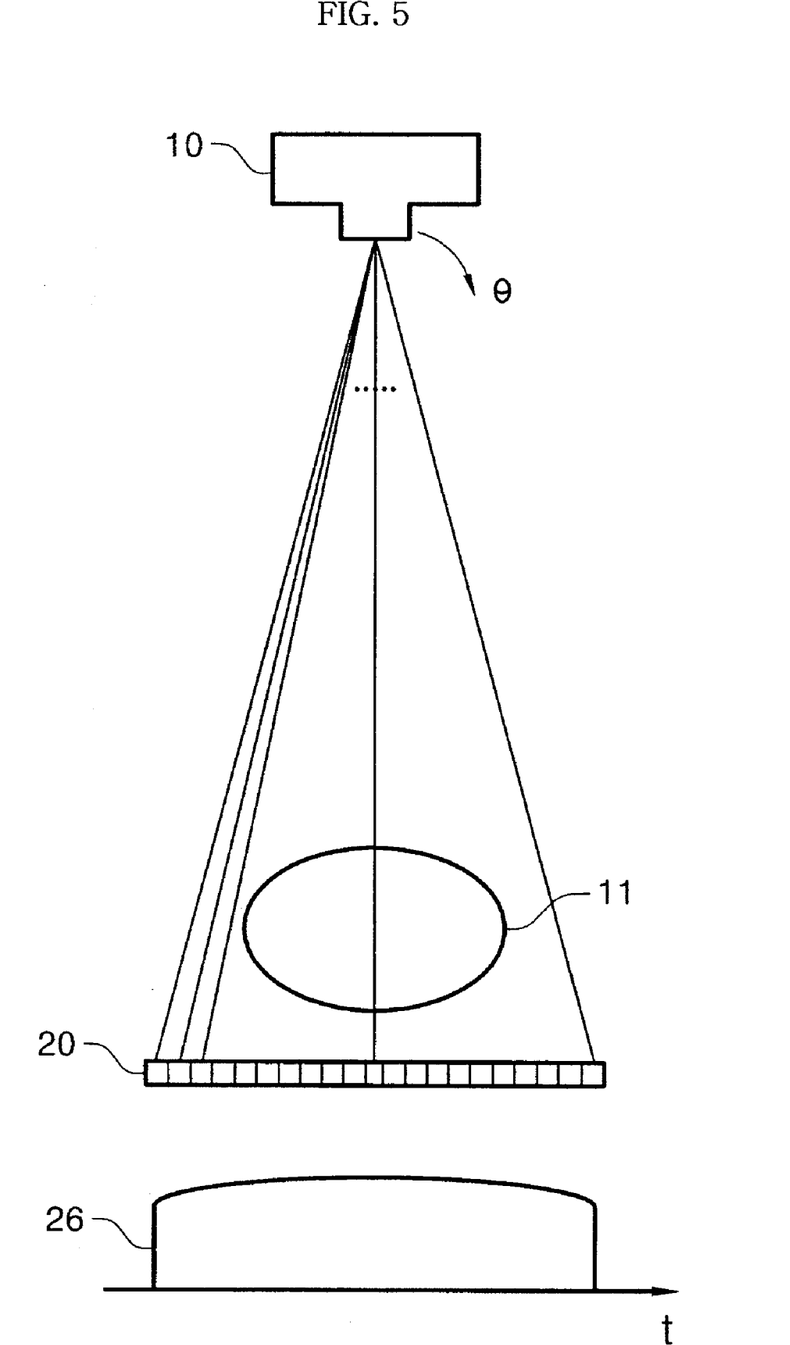
Figure 6:
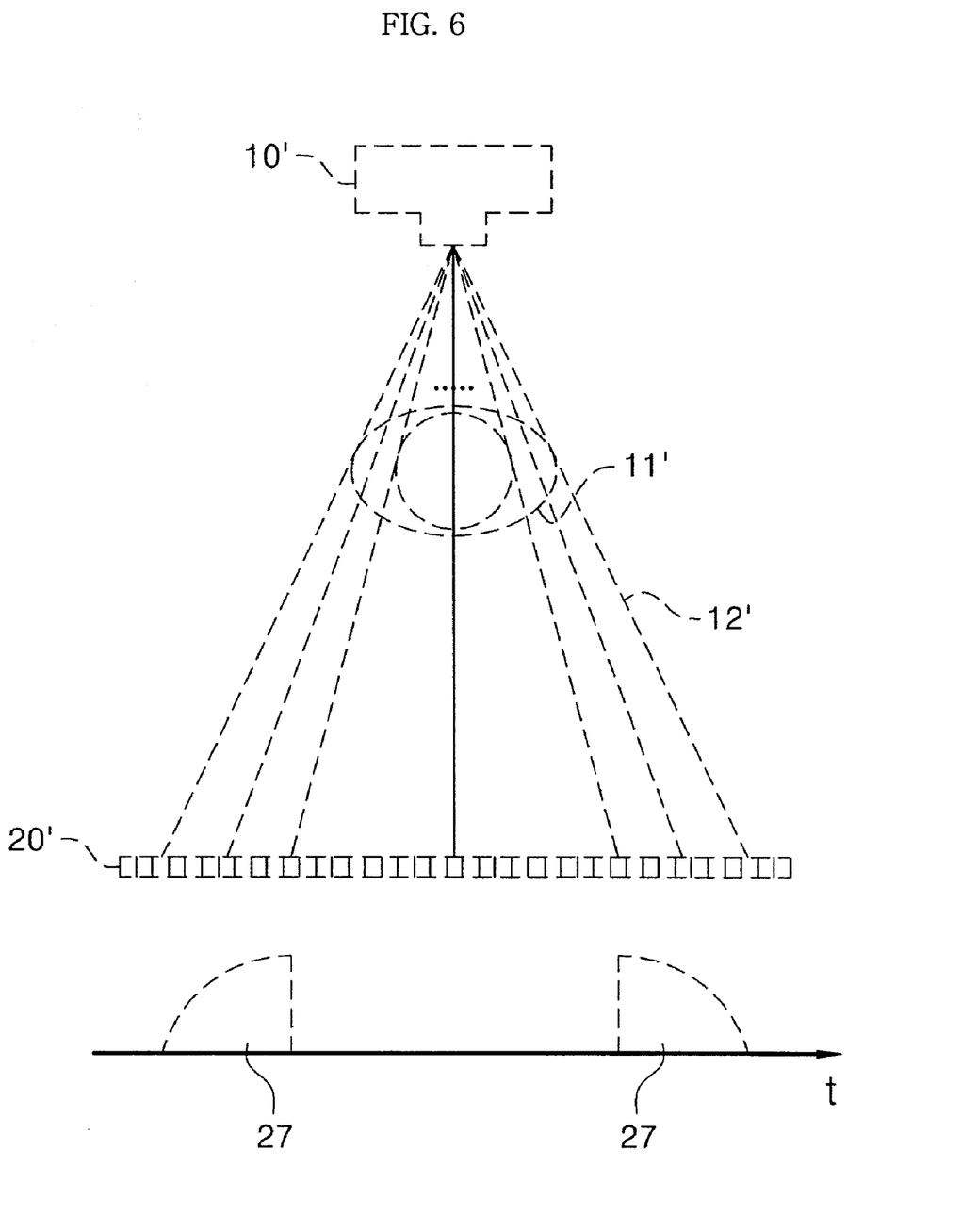
Figure 7:
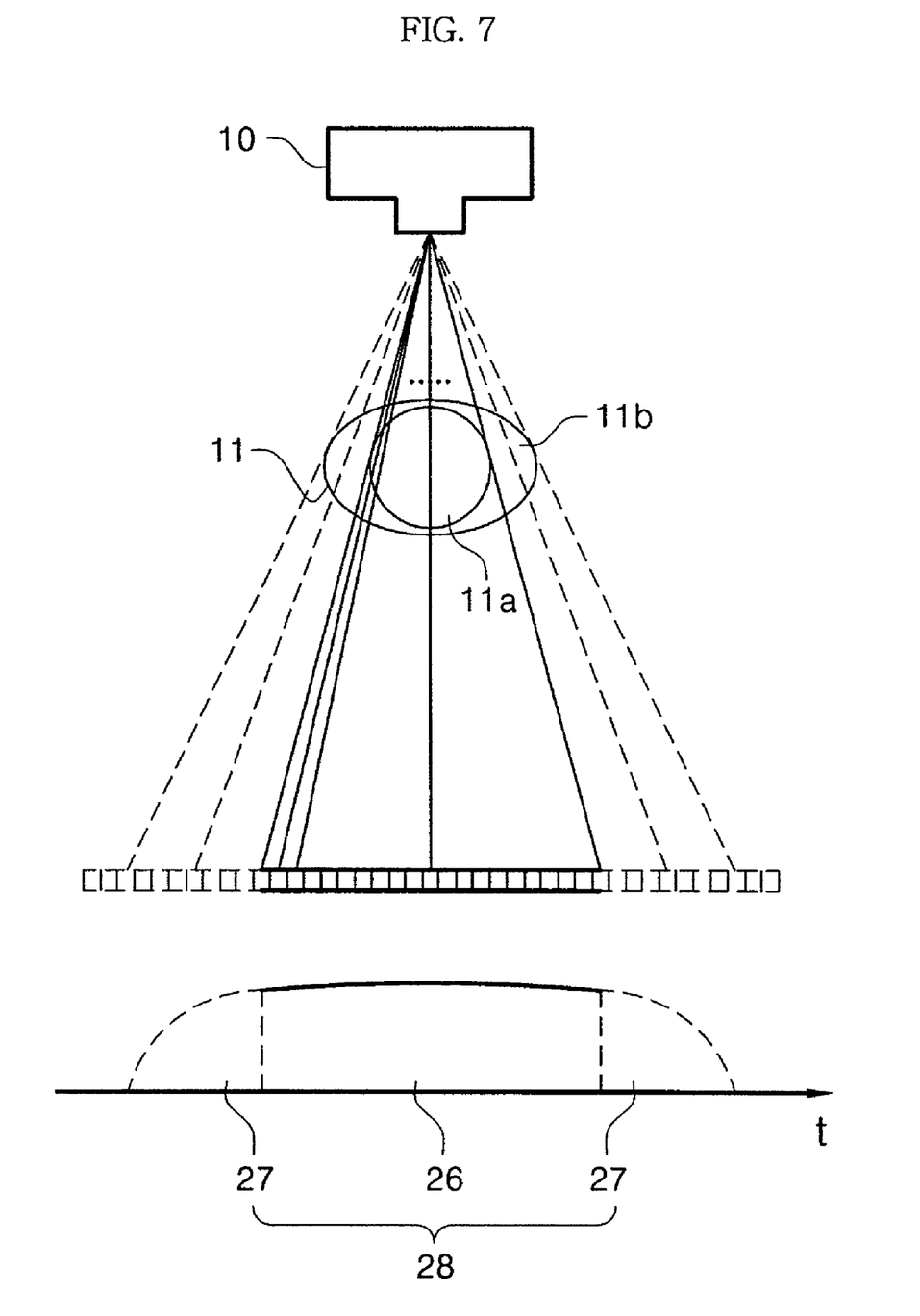

Next, in order to complement such a distortion phenomenon, the projection data on the portion 11b of the target object 11 existing outside the range of irradiation angles of X-rays are acquired as follows. That is, as shown in FIG. 5, the target object 11 is moved from the X-ray generator 10 toward the X-ray detector 20 such that the entire target object 11 is included within the range of irradiation angles of X-rays, and the X-rays are irradiated thereon, thereby acquiring low resolution projection data 26 through 360° scanning. Next, a CT image for the entire target object 11 is reconstructed based on the low resolution projection data 26 on the entire target object. The CT image obtained through the reconstruction based on the projection data acquired in the state shown in FIG. 5 has low resolution due to reduced magnification effects, but is a complete CT image without distortion since the entire target object is included within the range of irradiation angles of X-rays.

Then, projection data on the assumption that X-rays are irradiated on the target object at the same position as the case of FIG. 4 are calculated by a computer from the reconstructed low resolution CT image data. Subsequently, projection data on the portion existing outside the range of irradiation angles in FIG. 4 are extracted from the virtual projection data calculated by the computer and are then combined with the high resolution projection data on the portion within the range of irradiation angles, thereby acquiring projection data on the entire target object without distortion. This will be specifically described below with reference to FIGS. 6 and 7.

Figure 11:
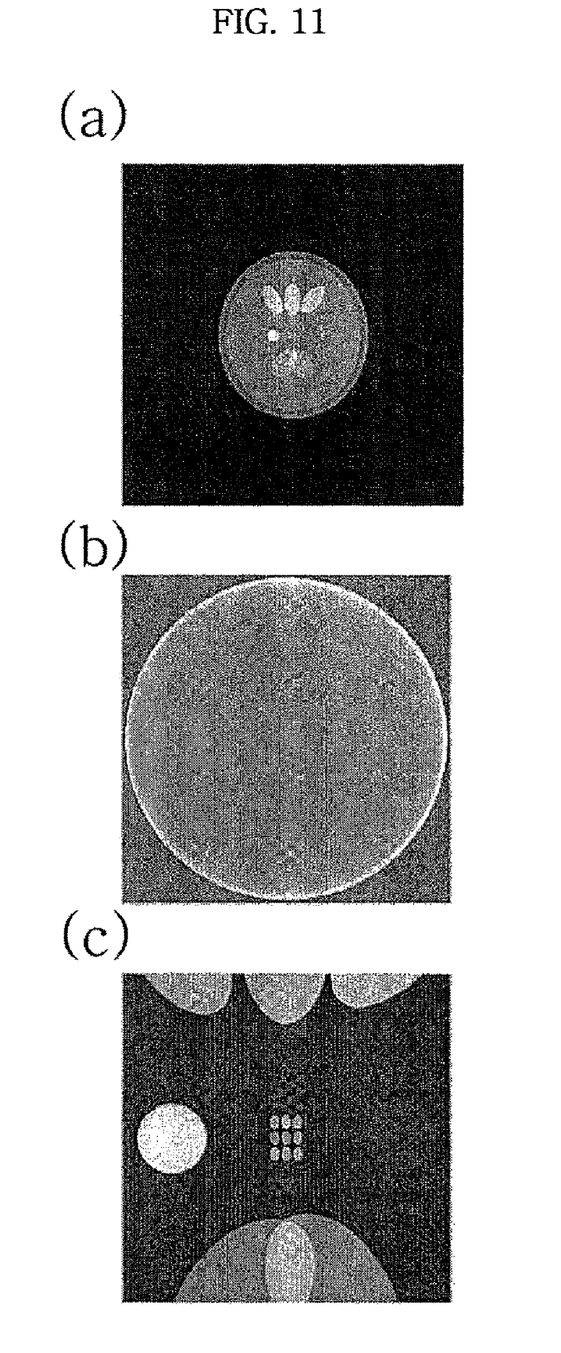
FIG. 11 shows local high resolution tomograms obtained by means of the method and apparatus according to an embodiment of the present invention.

First, assume that the projection data 26 acquired under the conditions shown in FIG. 5 are defined as $P_\theta^1(t)$, and the projection data 25 acquired under the conditions shown in FIG. 4 are defined as $P_\theta^2(t)$. As described above, the former is low resolution projection data on the entire target object, and the latter is high resolution projection data on a portion including the local region of interest 11a on the target object. Here, θ indicates a rotational angle around the target object, and t indicates coordinates along the length of the X-ray detector. Since $P_\theta^2(t)$ is projection data acquired in the state where the target object is not fully included within the range of irradiation angles of X-rays, reconstruction of an image based on these projection data causes data distortion. To complement this, $P_\theta^1(t)$ is used. First, a CT image is reconstructed using $P_\theta^1(t)$. In order to supplement the projection data on the portion of the target object existing outside the range of irradiation angles, virtual projection data 27 are acquired from a reconstructed CT image 11' shown in FIG. 6 on the assumption that X-rays are irradiated under the same geometrical conditions as $P_\theta^2(t)$. The method for acquiring the virtual projection data 27 on the portion existing outside the range of irradiation angles is performed using a virtual X-ray generator 10' and a virtual X-ray detector 20' in a virtual space defined by a computer. The virtual projection data 27 are acquired from the CT image 11' obtained in FIG. 5 by performing line integral for the values of image pixels through which virtual X-rays 12' pass. This directly uses a principle by which upon passage of actual X-rays through an object, values attenuated according to the physical property and length of the object are subjected to line integral and then detected by an X-ray detector. As compared with the actual X-ray generator 10, the virtual X-ray generator 10' used in this case is assumed to have a range of irradiation angles for allowing projection data on the entire target object to be included. The projection data acquired through the calculation are defined as $P_\theta^r(t)$. The virtual projection data acquired through the calculation have low resolution but have information on the portion of the target object existing outside the range of irradiation angles. Therefore, when two pieces of projection data $P_\theta^2(t)$ and $P_\theta^r(t)$ are combined with each other according to the following equation, it is possible to acquire new projection data 28, which have high resolution at the local region of interest 11a on the target object and low resolution at the portion 11b except the local region of interest, as shown in FIG. 11.

$$P_\theta^C(t) = \begin{pmatrix} P_\theta^2(t) & -\frac{t_m}{2} \leq t \leq \frac{t_m}{2} \\ P_\theta^r(t) & |t| \geq t_m \end{pmatrix} \quad (6)$$

When the projection data thus acquired are reconstructed by means of a general method for reconstructing a CT image, it is possible to obtain an image that has high resolution at a local region of interest without distortion. FIG. 11 shows cross-sectional images reconstructed by means of the method for reconstructing a CT image including a high resolution X-ray CT image for a local region of interest according to an embodiment of the present invention. FIG. 11 (a) is a tomogram of an image obtained by reconstructing $P_\theta^1(t)$ (in the tomogram, a portion designated by a dotted line is a local region of interest that is desired to be reconstructed with high resolution), and FIG. 11 (b) is a tomogram of an image obtained by reconstructing $P_\theta^2(t)$. As described above, image distortion is observed in FIG. 11 (b). FIG. 11 (c) is a tomogram of an image reconstructed by means of the method proposed by an embodiment of the present invention. It can be understood that a high resolution image for a local region of interest can be obtained without distortion according to the method of an embodiment of the present invention. Further, the method proposed by an embodiment of the present invention is applicable to an X-ray detector constructed either in a one-dimensional arrangement or in a two-dimensional arrangement.

Figure 8:
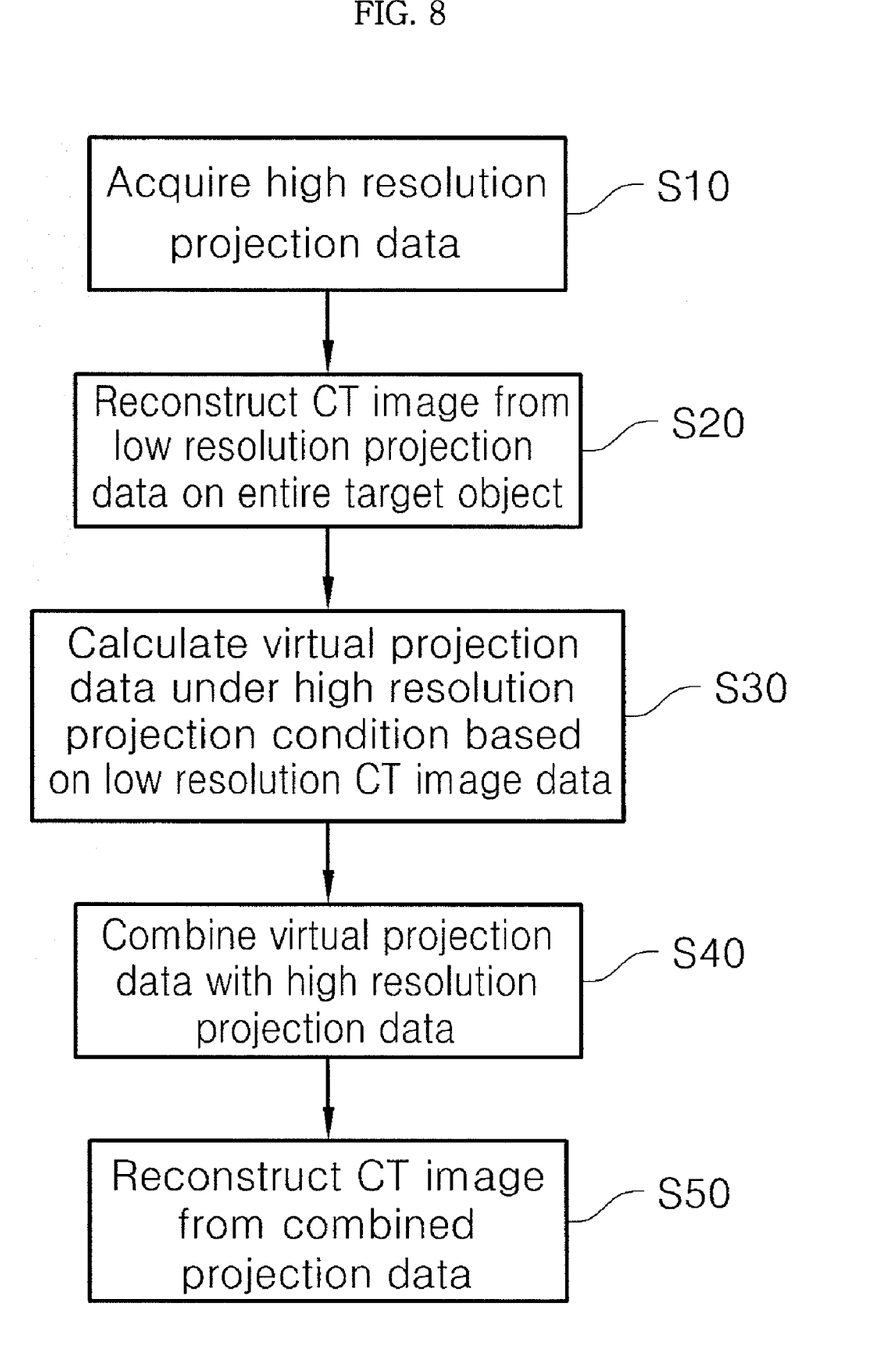
FIG. 8 is a flowchart illustrating a method for reconstructing a local high resolution X-ray CT image according to an embodiment of the present invention.

FIG. 8 is a flowchart illustrating a method for obtaining a local high resolution X-ray CT image according to an embodiment of the present invention (the method for reconstructing a high resolution image according to an embodiment of the present invention will be referred to as "zoom-in method"). First, low resolution projection data are acquired to obtain a cross-sectional image by means of general tomography. Then, high resolution projection data on a local region of interest on a target object are acquired (S10). Subsequently, a low resolution CT image is reconstructed from low resolution projection data on the entire target object (S20). Thereafter, based on data on the low resolution CT image, virtual projection data are calculated under conditions for high resolution (S30). Then, the low resolution virtual projection data are combined with the high resolution projection data (S40). Then, a CT image is reconstructed from the combined projection data, thereby obtaining a CT image without distortion.

Next, an embodiment of an apparatus for obtaining a local high resolution X-ray CT image according to an embodiment of the present invention will be described with reference to FIGS. 9 and 10.

Figure 9:
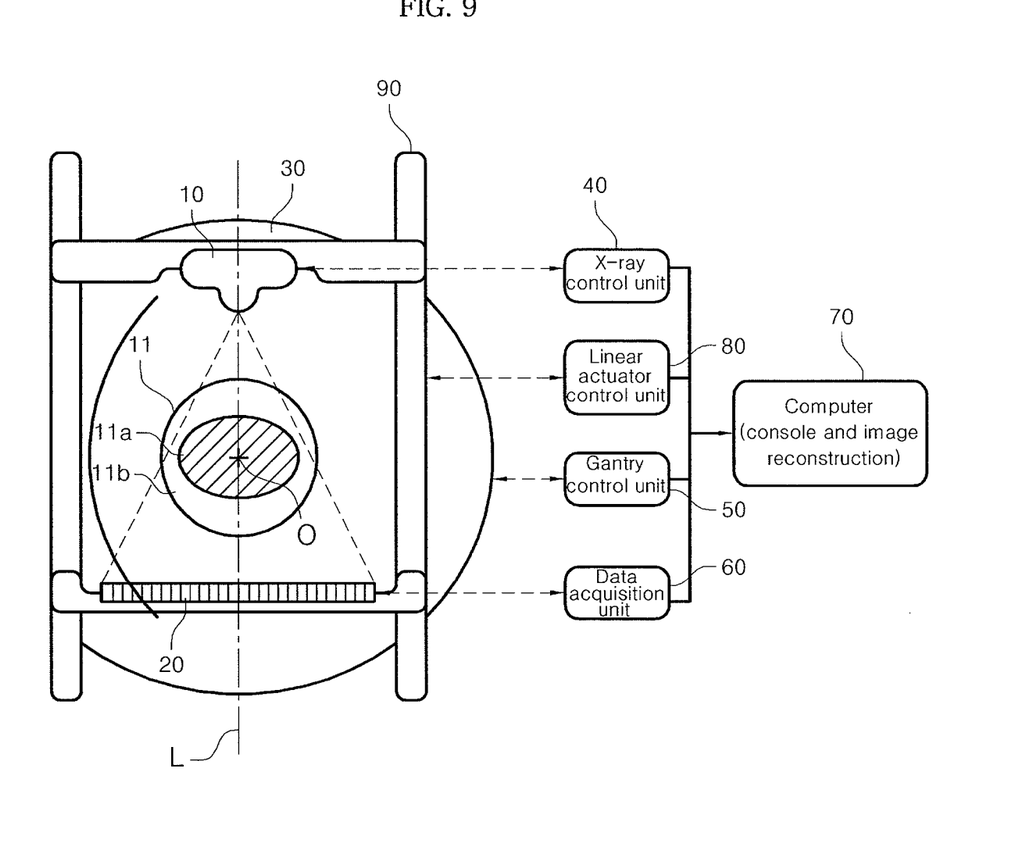
FIG. 9 is a schematic view showing an embodiment of an apparatus for reconstructing a local high resolution X-ray CT image according to an embodiment of the present invention.

Referring to FIG. 9, an apparatus for reconstructing an X-ray CT image according to an embodiment of the present invention comprises a rotatably installed gantry 30, a linearly moving means 90 secured on the gantry 30, and an X-ray generator 10 and an X-ray detector 20 movably installed at opposite positions on the linearly moving means 90. The X-ray detector 20 detects X-rays that have been radiated from the X-ray generator 10 and passed through a target object, and outputs projection data. Further, the apparatus for reconstructing an X-ray CT image comprises an imaging system for reconstructing an image for the target object by receiving the projection data from the X-ray detector 20. The imaging system comprises a data acquisition unit 60 for acquiring the projection data, a computer 70 for performing image reconstruction, and a display means (not shown) for displaying a reconstructed image thereon. In addition, the apparatus for reconstructing an X-ray CT image comprises a gantry control unit 50 for controlling the operation of the gantry 30, an X-ray control unit 40 for controlling the X-ray generator 10, and a linear actuator control unit 80 for controlling the linearly moving means 90.

The linearly moving means 90 is configured to move the X-ray generator 10 relative to the target object 11 along a line L that passes through a rotational center O of the gantry. Further, the linearly moving means 90 is configured to simultaneously move the X-ray generator 10 and the X-ray detector 20 such that they are not moved relative to each other. The linearly moving means 90 is preferably a ball screw and a servomotor but is not limited thereto. The apparatus for reconstructing an X-ray CT image according to this embodiment is different from a typical conventional apparatus in that contrary to the typical apparatus in which the X-ray generator 10 and the X-ray detector 20 are secured on the gantry 30 to be simply rotated around the target object 11, they can be moved relative to each other by the linearly moving means along the line L with respect to the gantry. Moreover, the linearly moving means 90 is secured on the gantry 30 so that it can be rotated together with the gantry 30 around the target object.

That is, the distance between the target object 11 and the X-ray generator 10 can be controlled while consistently maintaining the distance between the X-ray generator 10 and the X-ray detector 20, so that the resolution of an image can be controlled by means of magnification effects. As described above, when the target object approaches the X-ray generator 10, a high resolution image can be obtained by means of the magnification effects. On the contrary, when the target object is moved away from the X-ray generator 10 and approaches the X-ray detector 20, a low resolution image can be obtained due to reduced magnification effects.

In an existing apparatus for reconstructing an X-ray CT image with a gentry structure, a high resolution image can be obtained by causing a target object to approach an X-ray generator. However, since there is a limitation on the size of the target object, the target object is generally placed at the center between the X-ray generator and the X-ray detector. Further, an obtained image is magnified using digital zooming, i.e., interpolation. This is simply magnify the size of the image without improvement of the resolution of the image, resulting in a disadvantage in that contrary to a high resolution image, it is not possible to grasp a detailed structure of the target object. However, with the use of the apparatus of an embodiment of the present invention, it is possible to overcome a problem of limited size, which occurs in case of high resolution imaging, and simultaneously to reconstruct a high resolution image for a local region on the target object without distortion, using the zoom-in method.

Figure 10:
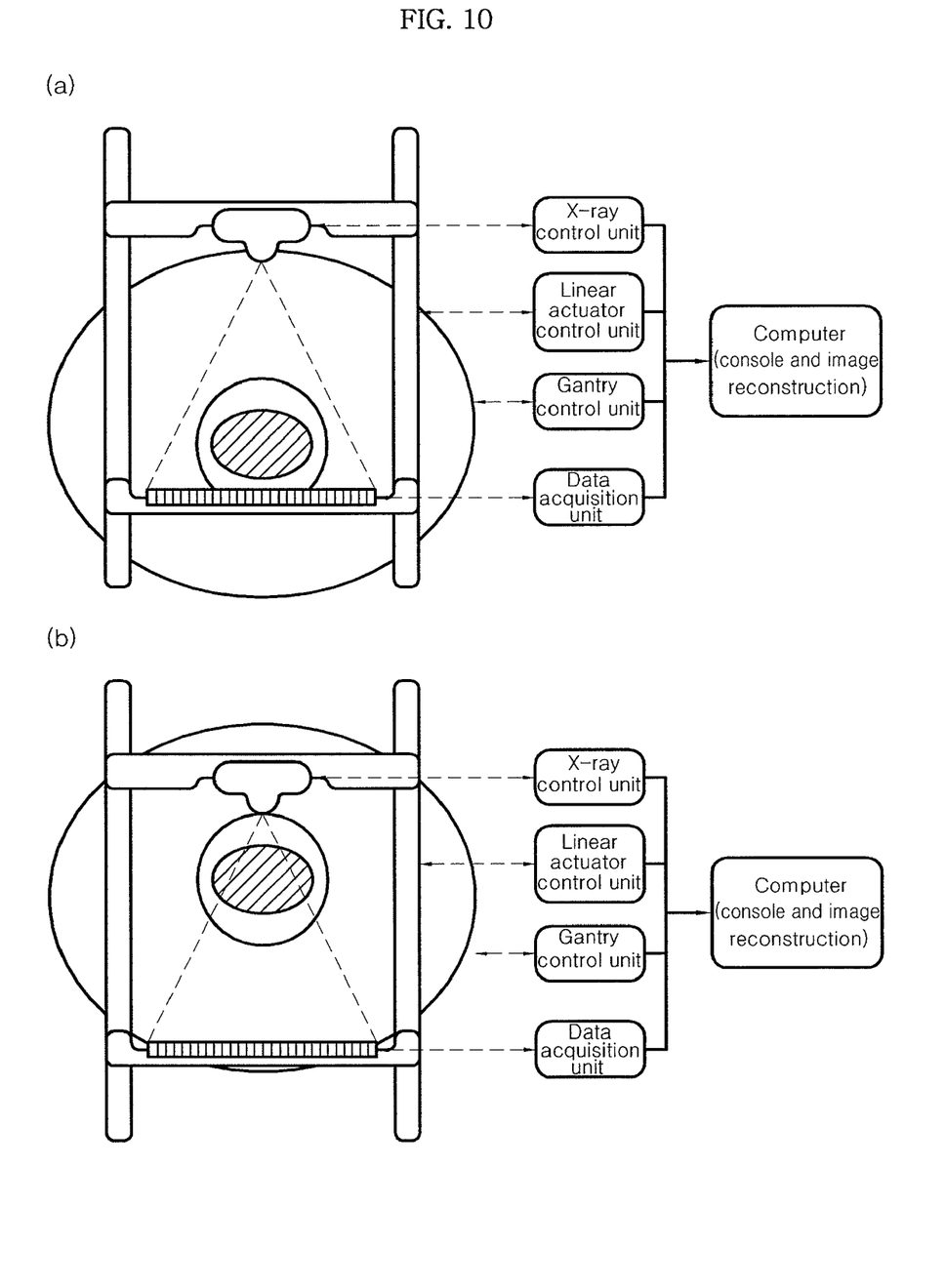
FIG. 10 is a schematic view illustrating the procedure for reconstructing a local high resolution X-ray CT image using the apparatus of FIG. 9.

FIG. 10 illustrates a method for using the apparatus of FIG. 9 to reconstruct a high resolution cross-sectional image for a local region of interest according to an embodiment of the present invention described above. When only a relative distance between the X-ray generator and the target object is simply changed so far as the entire target object 11 is included within a range of irradiation angles defined by the X-ray generator 10, it is possible to reconstruct a CT image while finely controlling the resolution of the entire target object. If it is intended to reconstruct a high resolution image for the local region of interest 11a to such an extent that the target object approaches the X-ray generator to cause a portion of the target object to deviate from the range of irradiation angles, low resolution projection data are acquired at a position shown in FIG. 10 (*a*), and high resolution projection data are sequentially acquired at a position shown in FIG. 10 (*b*).

Then, the computer 70 of the imaging system combines the high resolution projection data with the low resolution projection data according to the method described with reference to FIGS. 4 to 8, thereby reconstructing a high resolution image for the local region of interest without distortion. According to an embodiment of the present invention, there is provided a method and apparatus capable of reconstructing an image for a local region of interest without distortion by combining high resolution projection data with low resolution projection data.

In an apparatus for reconstructing an X-ray CT image according to an embodiment of the present invention, the distance between an X-ray generator and a target object can be controlled so that the resolution of an X-ray CT image can be controlled. Further, the apparatus for reconstructing an X-ray CT image according to an embodiment of the present invention can provide a local high resolution CT image without distortion by acquiring low resolution projection data for the entire target object and by acquiring high resolution projection data for a local region of interest while causing the target object to approach the X-ray generator.

It should not be construed that embodiments of the present invention described above and illustrated in the drawings limit the technical spirit of the present invention. The scope of the present invention should be defined only by the appended claims. It is apparent to those skilled in the art that various modifications and changes can be made thereto within the technical spirit of the invention. Therefore, the modifications and changes will fall within the scope of the present invention so long as they are apparent to those skilled in the art.

What is claimed is:

1. A method of tomographical imaging of an object, the method comprising:

providing a snapshot image data obtained in an X-ray projection to the object from a first relative location that is at a first distance from a point on the object and at a first orientation to the point on the object, wherein the snapshot image data comprises image information representing an interested portion of the object and at least one outside portion located outside the interested portion;

providing a tomographical image data obtained in an X-ray scan comprising a plurality of X-ray projections to the object from locations surrounding the object;

simulating an X-ray projection to the object from the first relative location using the tomographical image data, thereby generating a simulated snapshot image data comprising image information which represents another outside portion that is neither the interested portion nor the at least one outside portion; and constructing another tomographical image data of the interested portion using the snapshot image data and the simulated snapshot image data.

2. The method of claim 1, wherein the tomographical image data has a first resolution, wherein the other tomographical image data has a second resolution higher than the first resolution.

3. The method of claim 1, wherein the snapshot image data does not comprise image information representing the other outside portion.

4. The method of claim 1, wherein the simulated snapshot image data comprises image information representing at least part of the interested portion.

5. The method of claim 1, wherein constructing the other tomographical image data comprises:

combining the snapshot image data and the simulated snapshot image data to generate a combined snapshot image data of the object comprising image information that represents the interested portion, at least one outside portion and the other outside portion.

6. The method of claim 1, wherein providing the snapshot image data comprises:
scanning the object using an X-ray source rotating about the object at a first radius.

7. The method of claim 6, wherein providing the tomographical image data comprises:
scanning the object using the X-ray source or another X-ray source rotating about the object at a second radius greater than the first radius.

8. The method of claim 7, further comprising:
providing a machine comprising the X-ray source and an object support;
placing the object on the object support; and
moving the X-ray source toward or away from the object prior to or after scanning the object at the first radius.

9. The method of claim 1, wherein the object is a patient's body.

10. The method of claim 9, wherein the interested portion is an organ of the patient's body.

11. A method of tomographical imaging of an object, the method comprising:
scanning an object using an X-ray source rotating about the object at a first radius, thereby obtaining a first image data of the object, which comprises a snapshot image data representing the object taken in an X-ray projection from a first relative location that is at a first distance from a point of the object and a first orientation to the point, wherein the snapshot image data comprises image information representing an interested portion of the object and a first outside portion of the object located outside the interested portion;
scanning the object using the X-ray source or another X-ray source rotating about the object at the second radius greater than the first radius, thereby obtaining a second image data of the object;
processing the second image data, thereby constructing a simulated snapshot image data as if the simulated snapshot image data represents the object taken in an X-ray projection of the object from the first relative location, wherein the simulated snapshot image data comprises image information representing a second outside portion of the object other than the interested portion; and
combining the snapshot image data and the simulated snapshot image data to generate a combined snapshot image data of the object comprising image information that represents the interested portion, the first outside portion and the second outside portion.

12. The method of claim 11, wherein the first image data has a first resolution, wherein the second image data has a second resolution lower than the first resolution.

13. The method of claim 11, wherein the second image data comprises a tomographical image data.

14. The method of claim 11, wherein the snapshot image data does not comprise image information representing the second outside portion.

15. The method of claim 11, wherein the simulated snapshot image data comprises image information representing at least part of the interested portion.

16. The method of claim 11, further comprising:
constructing another tomographical image data of the interested portion using the combined snapshot image data.

17. The method of claim 11, wherein the second image data comprises a plurality of snapshot images of the object, each of which comprises image information representing the interested portion, the first outside portion and the second outside portion.

18. The method of claim 11, wherein the X-ray source has a radiation angle, wherein the second outside portion is located outside the radiation angle and the interested portion is located within the radiation angle when the X-ray source is projecting X-rays for the snapshot image data of the object at the first relative location.

19. The method of claim 11, further comprising:
providing a machine comprising the X-ray source and an object support;
placing the object on the object support; and
moving the X-ray source toward the object prior to scanning the object at the first radius.

20. The method of claim 11, wherein the object is a patient's body.

* * * * *